United States Patent
Akahoshi

(10) Patent No.: US 9,050,167 B2
(45) Date of Patent: Jun. 9, 2015

(54) INFUSION SLEEVE WITH LEAKAGE CONTROL

(75) Inventor: Takayuki Akahoshi, Tokyo (JP)

(73) Assignee: ART, LIMITED, Grand Cayman (KY)

( * ) Notice: Subject to any disclaimer, the term of this patent is extended or adjusted under 35 U.S.C. 154(b) by 0 days.

(21) Appl. No.: 13/029,827

(22) Filed: Feb. 17, 2011

(65) Prior Publication Data

US 2012/0191034 A1 Jul. 26, 2012

Related U.S. Application Data

(60) Provisional application No. 61/305,885, filed on Feb. 18, 2010.

(51) Int. Cl.
*A61F 9/007* (2006.01)
*A61M 1/00* (2006.01)

(52) U.S. Cl.
CPC .......... *A61F 9/00745* (2013.01); *A61M 1/008* (2013.01); *A61M 2210/0612* (2013.01)

(58) Field of Classification Search
CPC ........... A61B 17/320068; A61B 2017/320084; A61B 2017/320088; A61F 9/00736; A61F 9/00745; A61M 1/0058; A61M 1/0064; A61M 1/008; A61M 2210/0612
USPC ................... 604/22, 27, 35, 43, 167.06, 171; 606/107, 166–171
See application file for complete search history.

(56) References Cited

U.S. PATENT DOCUMENTS

| 5,873,851 A * | 2/1999 | Nilsson ........................ 604/43 |
| 6,117,151 A * | 9/2000 | Urich et al. ................. 606/169 |
| 6,997,908 B2 * | 2/2006 | Carrillo et al. ........... 604/167.06 |

* cited by examiner

*Primary Examiner* — Kami A Bosworth
(74) *Attorney, Agent, or Firm* — Wood, Phillips, Katz, Clark & Mortimer

(57) ABSTRACT

An irrigation sleeve for a phacoemulsification needle has a collar to limit leakage of irrigating liquid in a direction forward of the sleeve when the sleeve is positioned on the needle. In one embodiment the sleeve and needle have mating grooves and ridges. In another embodiment an O-ring embedded in the sleeve forms a seal against the needle body.

6 Claims, 3 Drawing Sheets

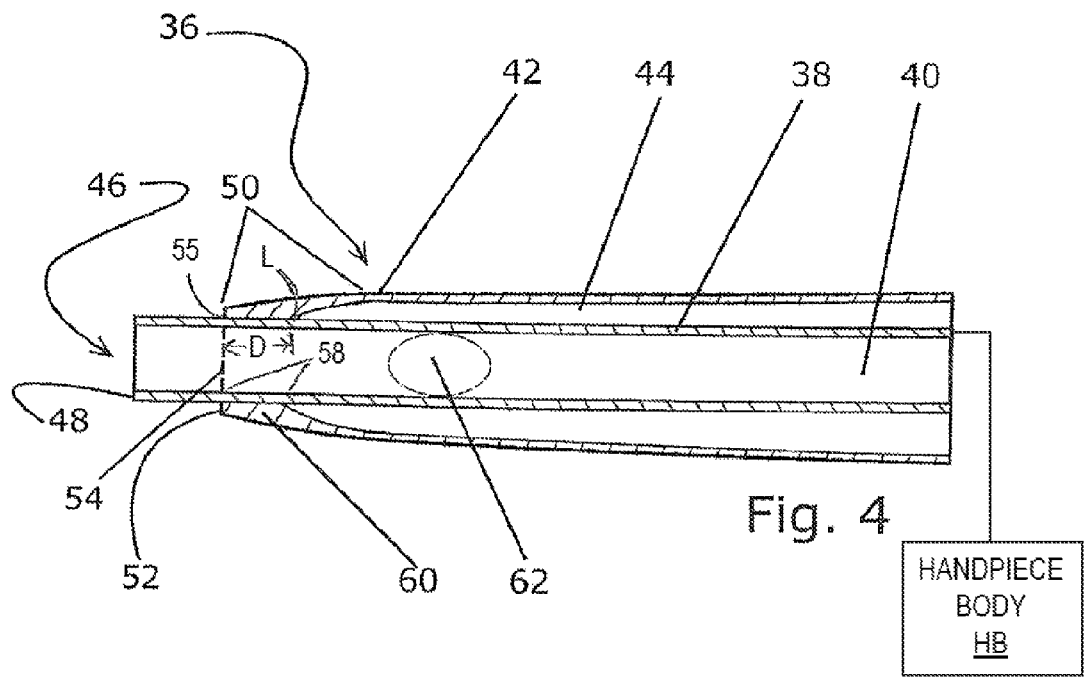
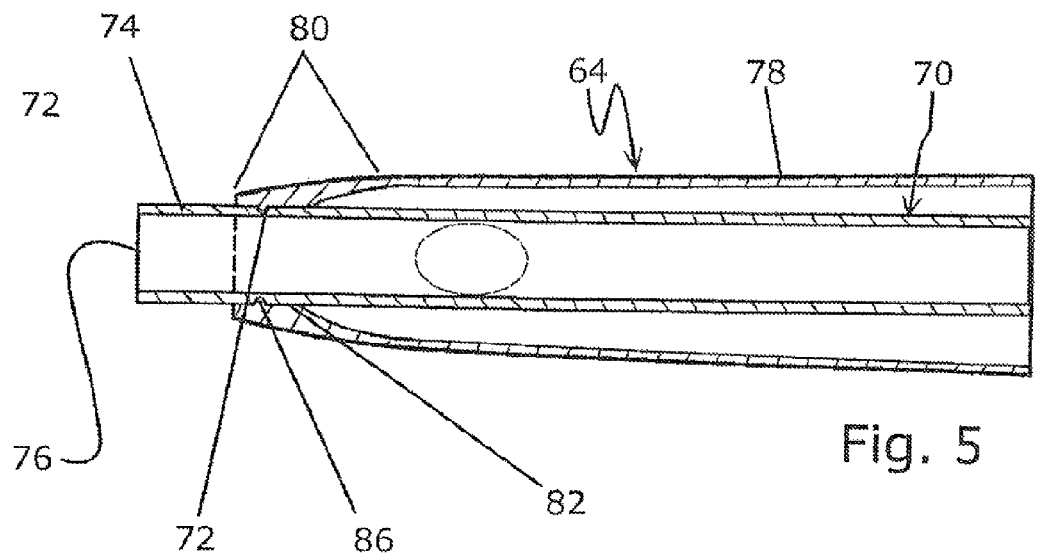

INFUSION SLEEVE WITH LEAKAGE CONTROL

BACKGROUND OF THE INVENTION

This application claims priority from U.S. Patent application Ser. No. 61/305,885, filed Feb. 18, 2010. and entitled "Infusion Sleeve with Leakage Control", which is incorporated herein in its entirety by reference.

This invention relates to surgical instruments and surgical techniques used in eye surgery and more particularly, to the technique of phacoemulsification apparatus and methods for their use.

A common ophthalmological surgical technique is the removal of a diseased or injured lens from the eye. Earlier techniques used for the removal of the lens typically required a substantial incision to be made in the capsular bag in which the lens is encased. Such incisions were often on the order of 12 mm in length.

Later techniques focused on removing diseased lenses and inserting replacement artificial lenses through as small an incision as possible. For example, it is now a common technique to take an artificial intraocular lens (IOL), fold it and insert the folded lens through the incision, allowing the lens to unfold when it is properly positioned within the capsular bag. Similarly, efforts have been made to accomplish the removal of the diseased lens through an equally small incision.

One such technique is known as phacoemulsification. A typical phacoemulsification tool includes a hollow needle to which electrical energy is applied to vibrate the needle at ultrasonic frequencies in order to fragment the diseased lens into small enough particles to be aspirated from the eye. Commonly, an infusion sleeve is mounted around the needle to supply irrigating liquids to the eye in order to aid in flushing and aspirating the lens particles.

It is extremely important to properly infuse liquid during such surgery. Maintaining a sufficient amount of liquid prevents collapse of certain tissues within the eye and attendant injury or damage to delicate eye structures. As an example, endothelial cells can easily be damaged during such collapse and this damage is permanent because these cells do not regenerate. One of the benefits of using as small in incision as possible during such surgery is the minimization of leakage of liquid during and after surgery and the prevention of such a collapse During phacoemulsification any aspiration liquid directed by the sleeve in a forward direction tends to repulse emulsified lens particles. Repulsion makes the phacoemulsification process less efficient and requires the surgeon to move the needle to bring the aspiration port on the needle close enough to the particles to aspirate them.

There are known prior art designs of sleeves with ports that are arranged to deliver irrigating liquid in a direction other than straight forward. However, a source of forward flow is the leakage of irrigating liquid through the forward portion of the sleeve between the sleeve and the outer needle surface.

Instruments using various types of infusing sleeves are well known and well-represented in the art and exemplify the attempts made by others to address the problem of maintaining an adequate flow of irrigating liquid without causing damage to the eye.

U.S. Pat. No. 4,643,717 (Cook et al) teaches and describes an aspiration fitting adapter formed as a sleeve concentric to the phaco needle and having a pair of bilaterally opposed discharge ports formed proximate the end of the sleeve to infuse irrigating liquid into the eye.

U.S. Pat. No. 5,151,084 (Khek) teaches and describes an ultrasonic needle with an infusion sleeve that includes a baffle. The sleeve of Khek also fits concentrically about the needle and allows the needle to protrude a substantial distance therefrom while providing pair of discharge ports bilaterally opposed to each other near the terminus of the sleeve.

U.S. Pat. No. 6,117,151 (Urich et al) teaches and describes an eye incision temperature protection sleeve fitted concentrically about a needle and having a single discharge port through which irrigating liquid is passed.

U.S. Pat. No. 6,605,054 (Rockley) teaches and describes a multiple bypass port phaco tip having multiple aspiration ports and a single discharge port to infuse liquid into the eye.

U.S. Pat. No. 5,879,356 (Geuder) teaches and describes a surgical instrument for crushing crystalline eye lenses by means of ultrasound and for removing lens debris by suction which demonstrates the use of a sleeve positioned concentric to the needle and having a pair of discharge ports formed thereon.

A series of patents issued to Richard J. Mackool illustrates further variations of irrigating sleeves. Mackool forms the sleeve with a somewhat flattened cross-section configuration intended to more closely approximate the shape of the incision through which the sleeve is inserted into the eye. This cross-section can be seen at FIG. 3 of U.S. Pat. No. 5,084,009.

U.S. Pat. No. 5,084,009 (Mackool) teaches and describes a liquid infusion sleeve for use during eye surgery with the sleeve having a flattened cross-section and having a pair of infusion ports formed on the forward portion of the flattened section.

U.S. Pat. No. 5,286,256 (Mackool) teaches and describes a liquid infusion sleeve having a free-floating rigid sleeve surrounding a needle which is intended to prevent the outer flexible sleeve from collapsing onto the needle.

U.S. Pat. No. 5,354,265 (Mackool) teaches and describes a liquid infusion sleeve showing yet another construction intended to keep the outer flexible infusion sleeve from collapsing onto the vibrating needle.

U.S. Pat. No. 5,505,693 (Mackool) teaches and describes a method and apparatus for reducing friction and heat generation by an ultrasonic device during surgery incorporating a needle support to prevent collapse of the outer flexible sleeve.

The Mackool patents are characterized by a pair of discharge ports formed at the distal end of the sleeve through which irrigating liquid is passed into the eye during the operation.

U.S. Pat. No. 5,645,530 (Boukhny) teaches and describes a phaco emulsification sleeve, one variation of which has a bellows portion attached to a discharge port ring which directs an annular flow of liquid around the needle and into the eye. The use of the bellows is intended to allow the sleeve to absorb spikes in liquid pressure during the operation.

U.S. Pat. No. 5,634,912 (Injev) teaches and describes an infusion sleeve having a rotating tip to allow the phaco needle to be repositioned during surgery. The top also has a single discharge port for infusing liquid during surgery.

Published U.S. Patent Application No. 2003/0004455 (Kadziauskas) teaches and describes a bi-manual phaco needle using separate emulsification and aspiration needles inserted into the eye simultaneously during surgery.

While the foregoing references describe the problems faced during phacoemulsification with respect to supplying the eye with an adequate amount of irrigating liquid, they do not particularly point out nor describe apparatus nor methods for limiting the forward leakage of irrigating liquid during phacoemulsification.

Accordingly, a need exists for an improved infusion sleeve which allows for an adequate volume of liquid to be infused into the eye while limiting the forward leakage of said liquid. This is particularly important with sleeves allowing for increased flow of liquid which, in turn, places greater stress on the sleeve.

The need also exists for such improved infusion sleeves to be simple in construction, efficient in operation and economical to manufacture.

In accordance with the preferred embodiment of the present invention, a phacoemulsification infusion sleeve has a thickened forward portion providing an enhanced barrier to forward leakage.

In another embodiment of the present invention, a ridge is formed on the internal surface of the forward portion of the phacoemulsification sleeve and a corresponding groove is formed on the exterior surface of the phacoemulsification needle. When the sleeve is applied to the needle, the ridge is seated in the groove.

In accordance with another preferred embodiment of the present invention, a ridge is formed on the external surface of the needle and a corresponding groove is formed on the internal surface of the sleeve. When the sleeve is applied to the needle, the ridge and groove seat to form a seal.

In accordance with another preferred embodiment, an O-ring or O-ring type insert is formed proximate the end of the sleeve and contacts the exterior surface of the needle when the sleeve is applied to the needle.

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

These and further aspects of the present invention will become apparent upon consideration of the accompanying drawing figures in which:

BRIEF DESCRIPTION OF THE DRAWINGS

FIG. 4 is a lateral sectional view of an irrigation sleeve embodying certain principles of the present invention;
FIG. 5 is a lateral sectional view of another embodiment of the sleeve shown in FIG. 4.

DETAILED DESCRIPTION OF THE DRAWINGS

Figure 1:
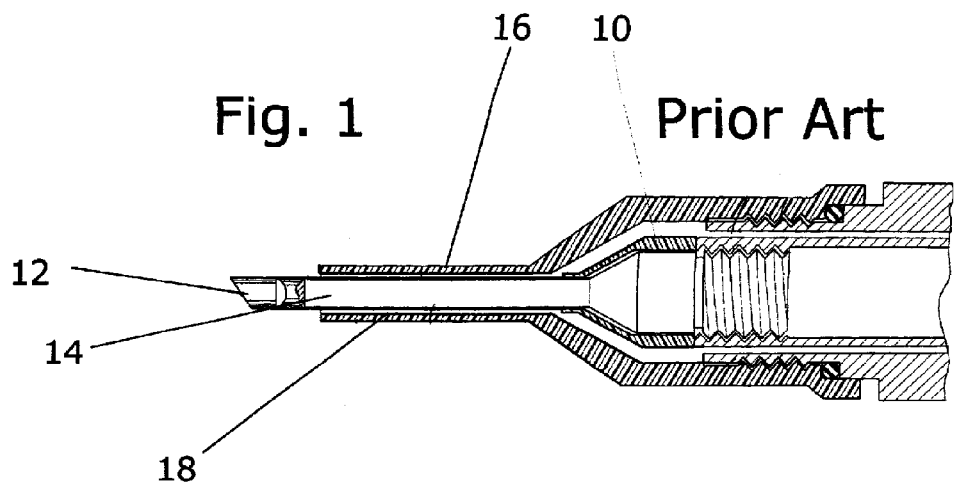
FIG. 1 is a first prior art illustration of a prior art irrigation sleeve.

Referring now to FIG. 1 the numeral 10 indicates generally a partial sectional view of a prior art phacoemulsification hand piece having a needle 12 defining a hollow internal chamber 14 through which irrigation liquid and emulsified particles of a lens are aspirated from the capsular bag. As seen in FIG. 1, an irrigating sleeve 16 is mounted to hand piece 10, from which needle 12 protrudes. Sleeve 16 communicates with an irrigation liquid supply within handpiece 10 and provides irrigating liquid to the capsular bag in a forward direction through an annular channel 18 formed between needle 12 and sleeve 16.

Figure 2:
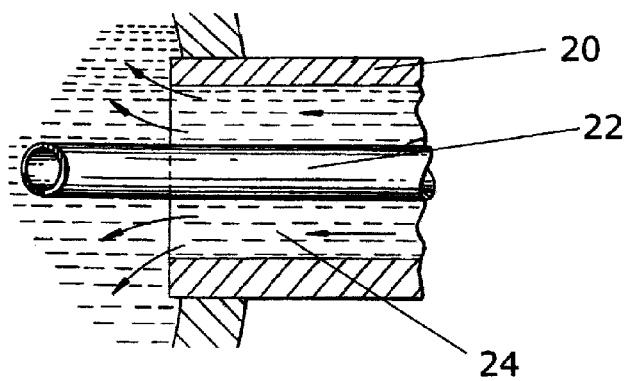
FIG. 2 is a second illustration of a prior art irrigation sleeve.

Referring now to FIG. 2, an enlarged partial sectional view of a second prior art phacoemulsification apparatus is shown having a sleeve 20 surrounding a hollow needle 22 and defining therebetween an annular channel 24 as a forward-directed conduit for irrigating liquid.

Both FIG. 1 and FIG. 2 show a prior art apparatus with the flow of irrigating liquid directed annularly about the periphery of the hollow phaco needle with the space available for flow being fixed in size and discharging liquid in a forward direction.

Figure 3:
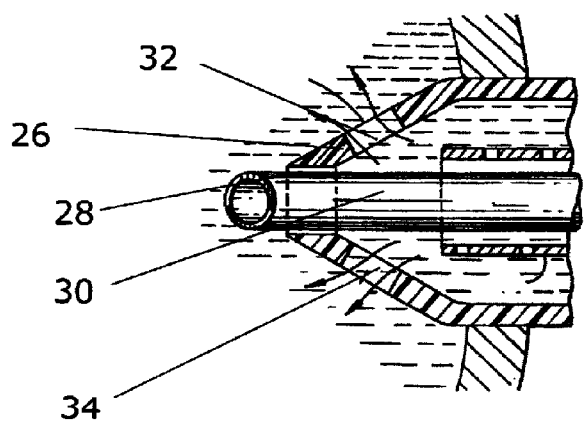
FIG. 3 is a third illustration of a prior art irrigation sleeve.

Referring now to FIG. 3, a partial sectional view of a second embodiment of the apparatus of FIG. 2 is shown where the infusion sleeve 26 tapers to form an opening 28 through which needle 30 extends. A pair of infusion ports 32, 34 are formed in the angled side walls of sleeve 26 to form a pathway for infusing liquid. Ports 32, 34 are fixed in size and shape. No provision is made to limit forward-flow leakage.

Referring now to FIG. 4, the numeral 36 identifies generally an irrigation sleeve positioned on a phacoemulsification needle 38 attached to and extending from a handpiece body HB. In the embodiment shown, needle 38 is a straight needle body having a central aspiration passageway 40. It is to be understood that the present invention can also be modified to work with phacoemulsification needles of varying shapes and configurations.

Sleeve 36 has a flexible tubular body/wall 42 defining a generally cylindrical liquid passageway 44. In the embodiment shown, passageway 44 is an annular space surrounding needle 38.

Needle 38 has an aspiration port 46 formed at one end thereof, defined by a needle lip 48. During phacoemulsification, a vacuum is applied to passageway 40 thereby drawing infused liquid and emulsified particles into passageway 40 by way of port 46.

As seen in FIG. 4, wall 42 has a generally uniform thickness throughout much of its length. A thickened tapered portion 50 is preferably formed on sleeve 36 beginning at that point 52 at which needle 38 protrudes from sleeve 36 and extending rearward until thickened portion 50 tapers down to join wall 42.

As seen in FIG. 4, tapered portion 50 terminates at sleeve mouth 54 defined by a sleeve lip 55. For purposes of description, sleeve 55 lip is considered to extend in a direction away from aspiration port 46 along a lengthwise distance D and to maintain a substantial uniform inside diameter to form a sleeve seat 58 over the length D. As seen in FIG. 4, seat wall portion 60 is locally thicker than the remainder of wall 42 and contacts the outer surface of needle 38. The distance D is substantially greater than the thickness of the sleeve wall 42 at the location at L where the wall 42 projects lengthwise away from the sleeve seat 58 toward the rearward end of the wall 42. It is these combined physical features that act to oppose the forward leakage of infusing liquid through annular space 44.

At least one port 62 is formed on sleeve 36 to allow infusing liquid to exit sleeve 36 and enter the eye.

It should be understood that the dimensions of seat 58 and the thickness of wall section 60 may be varied to provide for heightened resistance to forward leakage depending upon the volume and pressure of infusing liquid intended to be injected through sleeve 36.

Referring now to FIG. 5, a variation of the sleeve shown in FIG. 4 is described. In FIG. 5, a sleeve 64 is positioned on a needle 70. In a circumferentially extending groove 72 is formed on the outer wall surface 74 of needle 70, preferably proximate aspiration port 76.

Sleeve 64 has a sleeve wall 78 terminating at a thickened seat portion 80 having a seat 82 as hereinabove described with respect to FIG. 4. A radially-extending rib 86 is formed to project from seat 82 and is sized, shaped and positioned to engage groove 72 on needle 70 when sleeve 64 is positioned on needle 70. The seating of ridge 86 in groove 72 provides an added resistance to forward leakage.

Figure 6:
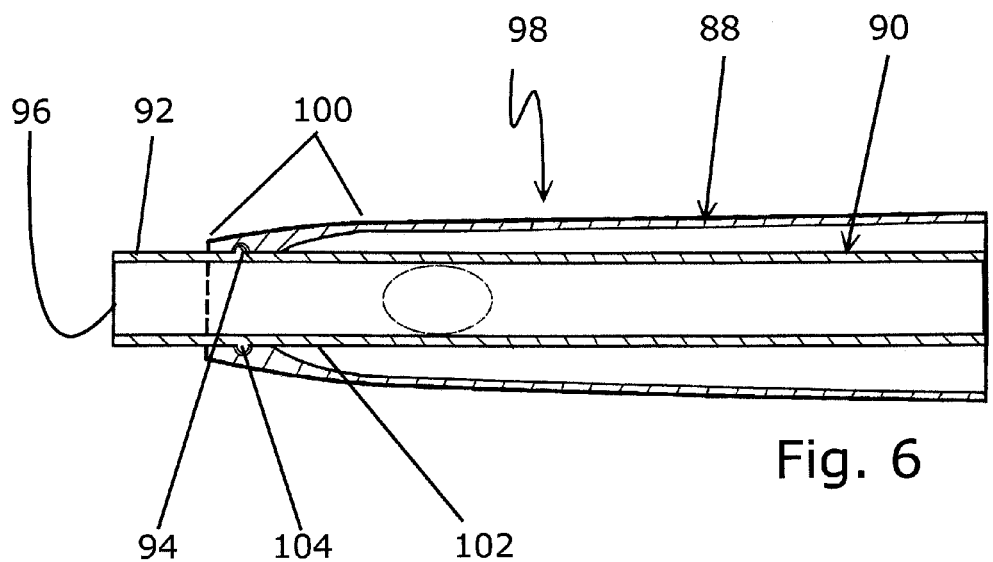
FIG. 6 is a lateral sectional view of another embodiment of the sleeve shown in FIG. 5.

Referring now to FIG. 6, a variation of the sleeve shown in FIG. 5 is illustrated.

Sleeve 88 is positioned on a phacoemulsification needle 90 having an outer wall surface 92. An upstanding circumferentially extending rib or ridge 94 extends radially outwardly from outer surface 92. Needle 90 terminates at an aspiration port 96.

In the embodiment shown, sleeve 88 has a wall 98 which terminates at a thickened seat wall portion 100. The interior surface 102 of which forms a seat and contact outer surface 92 of needle 90.

In the embodiment shown, a circumferentially extending groove 104 is formed at seat 102 and sized, shaped, and positioned to engage rib 94 when sleeve 88 is placed on needle 90. The engagement of rib 94 with groove 104 provides an added seal against forward leakage.

Figure 7:
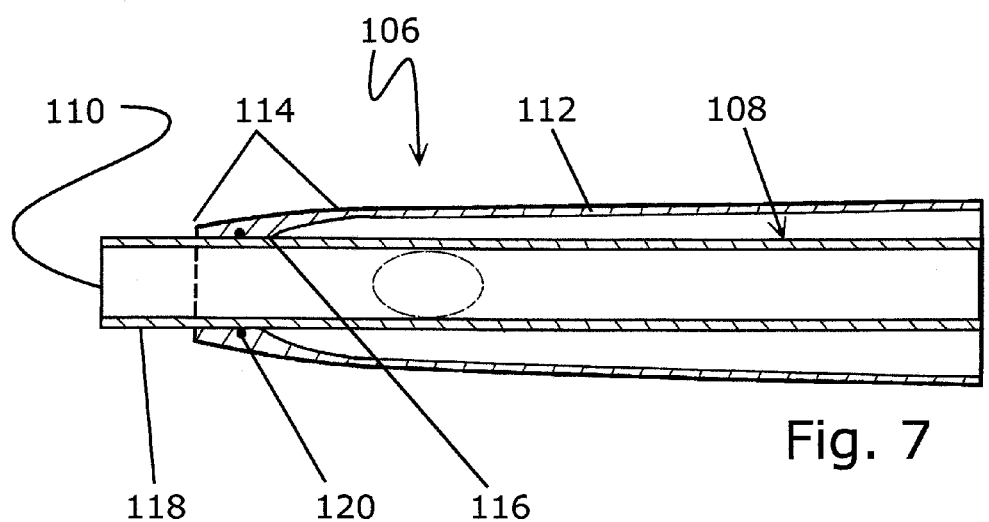
FIG. 7 is a lateral sectional view of another embodiment of the sleeve shown in FIG. 4.

Referring now to FIG. 7, yet another embodiment of sleeve shown in FIG. 4 is illustrated. Sleeve 106 is positioned on phacoemulsification needle 108 which terminates at an aspiration port 110.

Referring to FIG. 7, sleeve 106 is a wall 112 having a thickened seat portion 114 formed proximate aspiration port 110. Seat portion 114 has a seat 116 in contact with outer surface 118 of needle 108.

In the embodiment shown, an O-ring or O-ring type structure 120 is embedded in seat portion 115 and positioned such that a portion of the O-ring contacts outer surface 118 when sleeve 106 is positioned on needle 108. O-ring 120 also acts as an added preventive for forward fluid leakage.

It should be understood that in the embodiments shown in FIGS. 5 and 6, while a single groove ridge or rib is shown, any number of such ribs and grooves may be employed as deemed advantageous. It should also be understood that the length of seat portions such as 82, 102 and 116 may also be varied as needed.

With respect to FIG. 7, although a single O-ring structure has been shown, it is also possible to use more than one. With the structures of FIGS. 4 and 7, sleeves 36 and 106 may be positioned at a selected site along needle 108 while in the embodiments in FIGS. 5 and 6 position of the corresponding ribs and grooves will determine the position of the sleeve.

It is possible with the embodiments of FIGS. 5 and 6 to include a multiplicity of grooves combined with a single ridge to allow a degree of adjustablility for the position of a sleeve upon a phacoemulsification needle.

What is claimed is:

1. An infusion sleeve for use with a phacoemulsification handpiece, said handpiece having a hollow phacoemulsification needle attached to and extending from a handpiece body, said needle having an outer surface, said handpiece having a pathway through which irrigating liquid passes, said infusion sleeve comprising:
    a hollow tubular body with a length and a first, open end through which said needle is inserted,
    said tubular body having an outer surface and an inner surface and a thickness between the outer surface and the inner surface;
    a second end of the hollow tubular body having a tip,
    said tip having an opening through which said needle protrudes;
    said sleeve and said outer needle surface defining therebetween a passageway communicating with said liquid pathway to allow said liquid to pass into said sleeve when said sleeve is mounted to said handpiece;
    at least one port formed on said sleeve to allow said liquid to exit said passageway; and
    a locally thickened sleeve wall portion formed on said sleeve proximate said second sleeve end for preventing said liquid from discharging through said tip opening when said liquid flows through said sleeve,
    said locally thickened sleeve wall portion having an inner surface portion, sized and shaped to be in contact with said needle outer surface along a sleeve seat that extends over a first lengthwise distance when said sleeve is positioned on said handpiece,
    said first lengthwise distance substantially greater than the thickness of the tubular body at a location where the tubular body projects lengthwise away from the sleeve seat toward the first end of the hollow tubular body.

2. The infusion sleeve as recited in claim 1 further comprising
    a circumferentially-extending groove formed in said needle outer surface; and
    a circumferentially-extending rib formed on said inner surface of said sleeve,
    said groove and said rib sized, shaped and dimensioned to interengage at a position proximate said second sleeve end.

3. The infusion sleeve as recited in claim 1 further comprising
    a circumferentially-extending groove formed in said inner surface of said sleeve; and
    a circumferentially-extending rib formed on said needle outer surface,
    said groove and said rib sized, shaped and dimensioned to interengage at a position proximate said second sleeve end.

4. The infusion sleeve as recited in claim 1 wherein a circumferentially extending seal is interposed between the needle and tubular body at the locally thickened sleeve wall portion.

5. The infusion sleeve as recited in claim 4 wherein said seal is an O-ring.

6. The infusion sleeve as recited in claim 4 wherein the seal is embedded in the sleeve wall portion.

* * * * *